(12) United States Patent
Tanizaki

(10) Patent No.: US 9,297,674 B2
(45) Date of Patent: Mar. 29, 2016

(54) SENSOR HOUSING CONTAINER AND SENSOR ATTACHMENT METHOD USING SAME

(71) Applicant: PANASONIC HEALTHCARE HOLDINGS CO., LTD., Minato-ku, Tokyo (JP)

(72) Inventor: Yoichi Tanizaki, Ehime (JP)

(73) Assignee: PANASONIC HEALTHCARE HOLDINGS CO., LTD., Minato-Ku, Tokyo (JP)

( * ) Notice: Subject to any disclaimer, the term of this patent is extended or adjusted under 35 U.S.C. 154(b) by 11 days.

(21) Appl. No.: 14/388,240

(22) PCT Filed: Jun. 7, 2013

(86) PCT No.: PCT/JP2013/003595
§ 371 (c)(1),
(2) Date: Sep. 26, 2014

(87) PCT Pub. No.: WO2013/187031
PCT Pub. Date: Dec. 19, 2013

(65) Prior Publication Data
US 2015/0047431 A1 Feb. 19, 2015

(30) Foreign Application Priority Data

Jun. 11, 2012 (JP) ................................. 2012-131620
Apr. 9, 2013 (JP) ................................. 2013-080947

(51) Int. Cl.
*G01D 11/24* (2006.01)
*G01N 33/487* (2006.01)
*B65D 83/08* (2006.01)

(52) U.S. Cl.
CPC .......... *G01D 11/245* (2013.01); *B65D 83/0817* (2013.01); *G01N 33/48757* (2013.01); *Y10T 29/49826* (2015.01)

(58) Field of Classification Search
CPC .............................. G01D 11/24; G01D 11/245
USPC .......................................................... 73/431
See application file for complete search history.

(56) References Cited

U.S. PATENT DOCUMENTS

| 8,142,733 | B2 | 3/2012 | Creaven |
| 2008/0021296 | A1* | 1/2008 | Creaven ........... G01N 33/48757 |
| | | | 600/365 |

(Continued)

FOREIGN PATENT DOCUMENTS

| JP | 2001-281199 A | 10/2001 |
| JP | 2003-042994 A | 2/2003 |
| JP | 2006-347550 A | 12/2006 |
| JP | 2008-502901 A | 1/2008 |
| JP | 2008-518204 A | 5/2008 |
| JP | 4430195 B2 | 3/2010 |

(Continued)

OTHER PUBLICATIONS

International Search Report of Int'l Appln. No. PCT/JP2013/003595 issued on Jul. 9, 2013.

(Continued)

*Primary Examiner* — Lisa Caputo
*Assistant Examiner* — Jamel Williams
(74) *Attorney, Agent, or Firm* — Shinjyu Global IP

(57) ABSTRACT

A sensor housing container comprises a container having an opening, a lid that covers the opening, and a sensor housing body that can be pulled out of the opening of the container. The sensor housing body includes a sensor case, a plurality of sensors, and a spring that biases these sensors. The sensor case is provided with a sensor discharge port at the portion where the sensors are biased by the spring. Also, this sensor discharge port is provided with a guide protrusion for aligning the sensor discharge port with a sensor insertion port of a measurement device. Furthermore, the inner face of the container is provided with a push-out protrusion that contacts with the end of the sensors on the opposite side from electrodes, at the portion corresponding to the end of the sensors on the opposite side from the electrodes inside the sensor case.

18 Claims, 10 Drawing Sheets

(56) References Cited

U.S. PATENT DOCUMENTS

| | | | | |
|---|---|---|---|---|
| 2012/0312094 | A1* | 12/2012 | Uchida | G01C 19/5628 73/504.04 |
| 2014/0311931 | A1* | 10/2014 | Konishi | G01N 33/48757 206/363 |
| 2015/0047431 | A1* | 2/2015 | Tanizaki | G01N 33/48757 73/431 |
| 2015/0076016 | A1* | 3/2015 | Sato | B65D 51/24 206/305 |
| 2015/0136818 | A1* | 5/2015 | Tanizaki | G01N 33/48785 224/191 |

FOREIGN PATENT DOCUMENTS

| | | |
|---|---|---|
| JP | 4570290 B2 | 10/2010 |
| JP | 2012-001256 A | 1/2012 |
| JP | 2012-078109 A | 4/2012 |
| WO | 2006/009534 A1 | 1/2006 |

OTHER PUBLICATIONS

Office Action from the corresponding Japanese Patent Application No. 2014-520913 issued on Sep. 15, 2015.

* cited by examiner

SENSOR HOUSING CONTAINER AND SENSOR ATTACHMENT METHOD USING SAME

PRIORITY

This application claims priority to International Application PCT/JP2013/003595, with an international filing date of Jun. 7, 2013 which claims priority to Japanese Patent Application No. JP2012-131620 filed on Jun. 11, 2012 and Japanese Patent Application No. JP2013-080947 filed on Apr. 9, 2013. The entire disclosures of International Application PCT/JP2013/003595, Japanese Patent Application No. JP2012-131620, and Japanese Patent Application No. JP2013-080947 are hereby incorporated herein by reference.

TECHNICAL FIELD

The present invention relates to a sensor housing container that houses sensors for measuring blood glucose levels, for example, and to a sensor attachment method in which this container is used.

BACKGROUND

With a conventional sensor housing container, a plurality of thin sensors are housed in a sealed state in the interior of a cylindrical container. The user takes out one sensor from the container, mounts it to a blood glucose level measurement device, and measures the blood glucose level.

For elderly users, or those with limited vision, it can be difficult to take out a single sensor from a plurality of sensors housed in no order in a cylindrical container. The taken out container, which is thin, can also be difficult to insert into a sensor insertion port, which is formed as a slit to match the size of the sensor.

As a result, it is hard for the user to mount the sensors in the container properly to the measurement device, which makes the device less convenient to use.

In view of this, a sensor housing container has been proposed in which a single sensor is discharged from a container and inserted into the sensor insertion port of a measurement device (see Patent Literature 1: Japanese Unexamined Patent Application Publication (Translation of PCT Application) No. 2008-502901, for example).

However, all of the conventional sensor housing devices proposed so far have still been inconvenient to use. Specifically, with the sensor housing container in this conventional example, the user pushed a discharge trigger upon gripping the outer peripheral side face of the container, the electrodes of a single sensor were discharged from the container, and the electrodes were held in an exposed state on the container.

When the sensor held in the container is then inserted into a measurement device, the thin sensor, whose electrodes are exposed on the outside of the container, is not easy to connect properly to the measurement device. For example, the user holds the sensor housing container and slides the sensor with exposed electrodes into the sensor insertion port of the measurement device, but if the sensor is inserted at the wrong angle to the sensor insertion port, the thin sensor may bend and can be damaged. Also, the thin sensor will bend and be damaged if the user pushes the sensor housing container too hard against the measurement device.

In other words, it was still too difficult to mount a sensor in a measurement device, making the device inconvenient to use.

SUMMARY

The present invention comprises a container having an opening, a lid that openably and closeably covers the opening, and a sensor housing body that can be pulled out of the opening when the lid is open, the sensor housing body including a sensor case that can be pulled out of the opening. Also, there are a plurality of flat sensors that are stacked in the interior of the sensor case in a state in which the electrode side is on the opening side of the container, and a biasing body that biases the sensors stacked in the interior of the sensor case to one side. Also, the sensor case includes a sensor discharge port and a guide protrusion for aligning the sensor discharge port with a sensor insertion port of a measurement device. The sensor discharge port is provided to the portion where the sensors are biased by the biasing body on a face on the opening side of the container. The guide protrusion is provided to the portion of the sensor case on the outside of the sensor discharge port. Furthermore, on the inner face of the container, in a state in which the sensor case has been pulled out through the opening of the container, a push-out protrusion that comes into contact with the end of the sensors on the opposite side from the electrodes is provided to the portion inside the sensor case that corresponds to the end of the sensors on the opposite side from the electrodes.

As discussed above, the sensor housing container of the present invention is such that when the user opens the lid of the sealed container and pulls the sensor case out of the container, a sensor is disposed at a position opposite the sensor discharge port. The user then aligns the guide protrusion of the sensor case with the sensor insertion port of the measurement device, which forms a path for the sensor to move from the sensor case into the measurement device. In this aligned state, when the container is pressed one time to the measurement device side, this pressing action causes the push-out protrusion of the container to push a sensor in the sensor case out to the sensor discharge port side, and the pushed-out sensor goes through the sensor insertion path to be mounted at the specified location of the measurement device.

That is, the lid of the sealed container is opened and the sensor case housing the sensors is pulled out of the container. The guide protrusion of the sensor case is then aligned with the sensor insertion part of the measurement device, and the container is merely pressed against the measurement device, which allows a sensor to be mounted in the measurement device. The pulled-out sensor case is then put back into the container.

After this, the lid of the container is closed, which puts the remaining sensors back into a sealed state.

As a result, the user can easily mount a sensor housed in a sealed state in the container to a measurement device, and this makes the device more convenient to use.

DETAILED DESCRIPTION

Embodiments of the present invention will now be described through reference to the drawings, but the present invention is not limited by the following embodiments. It will be apparent to those skilled in the art from this disclosure that the following descriptions of the embodiments are provided for illustration only and not for the purpose of limiting the invention as defined by the appended claims and their equivalents.

First Embodiment

Figure 1:
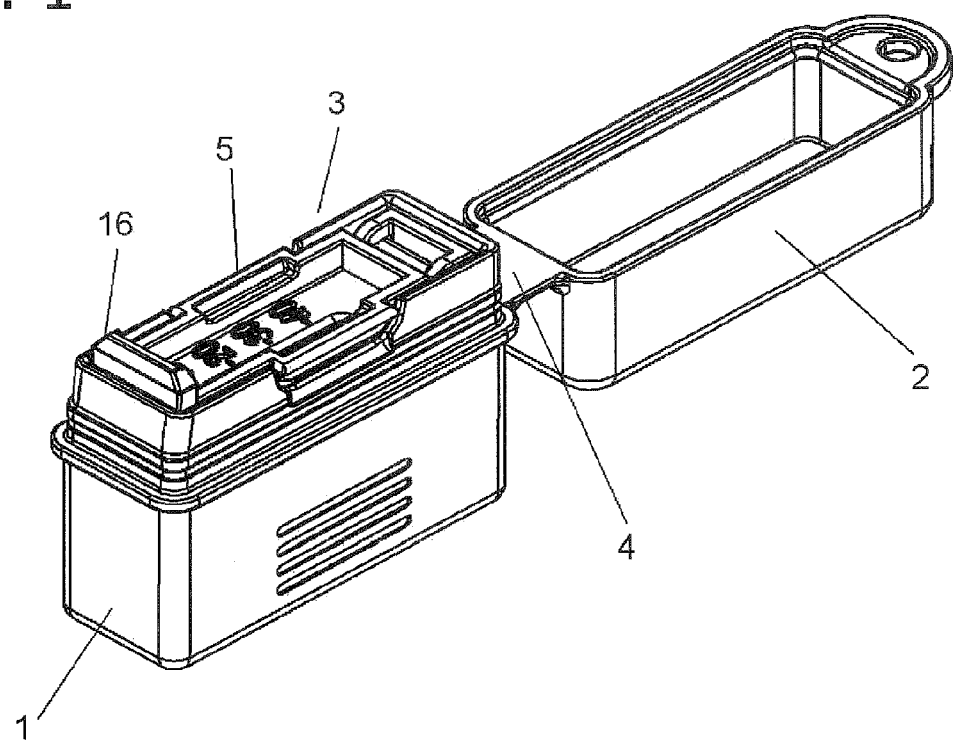
FIG. 1 is an oblique view of the sensor housing container pertaining to a first embodiment of the present invention.
Figure 2:
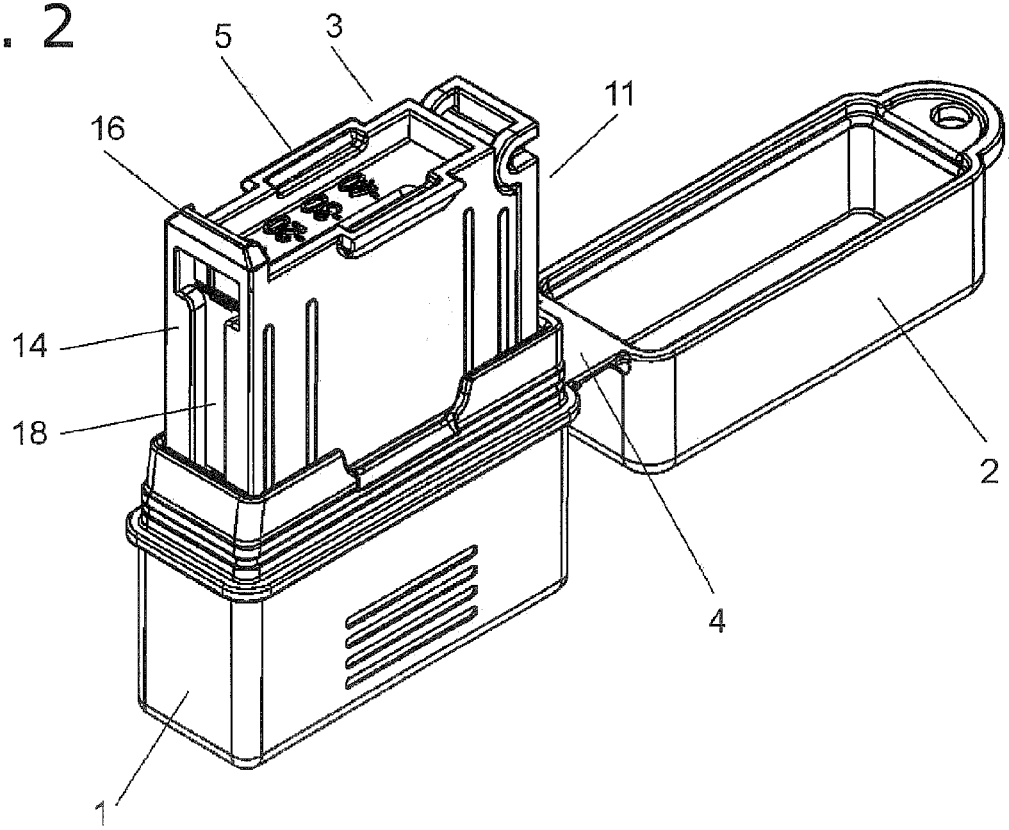
FIG. 2 is an oblique view of the sensor housing container pertaining to the first embodiment of the present invention.

As shown in FIGS. 1 and 2, the sensor housing container in the first embodiment of the present invention comprises a box-shaped container 1 having a rectangular opening in its upper face, a lid 2 that openably and closeably covers the opening in the container 1, and a sensor housing body 3 that is provided in the interior of the container 1 and can be pulled out through the opening of the container 1.

Figure 3:
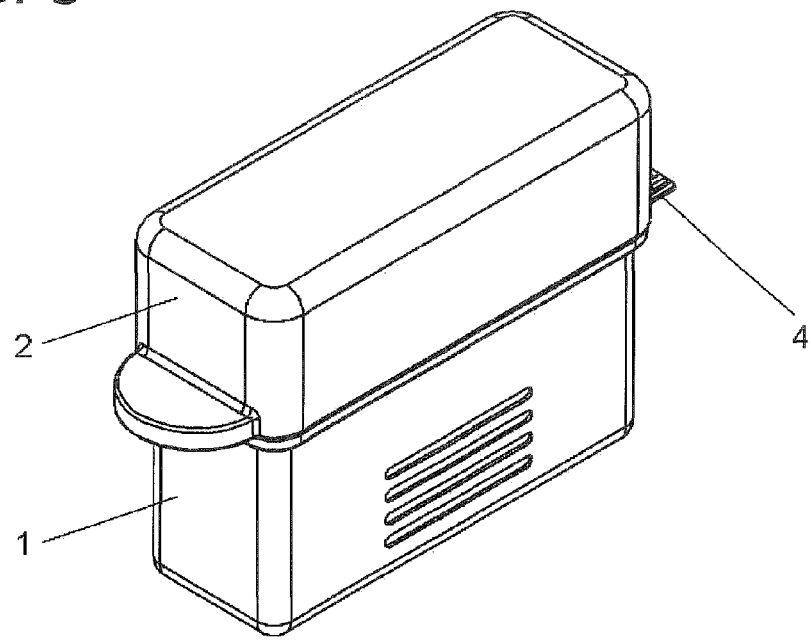
FIG. 3 is an oblique view of the sensor housing container pertaining to the first embodiment of the present invention.

The container 1 and the lid 2 are connected by a bendable connector 4, and are integrally molded from a synthetic resin along with the connector 4. As shown in FIG. 3, if the lid 2 is closed when the sensor housing body 3 has been pushed into the container 1, the interior of the container 1 is in a sealed state.

Figure 4:
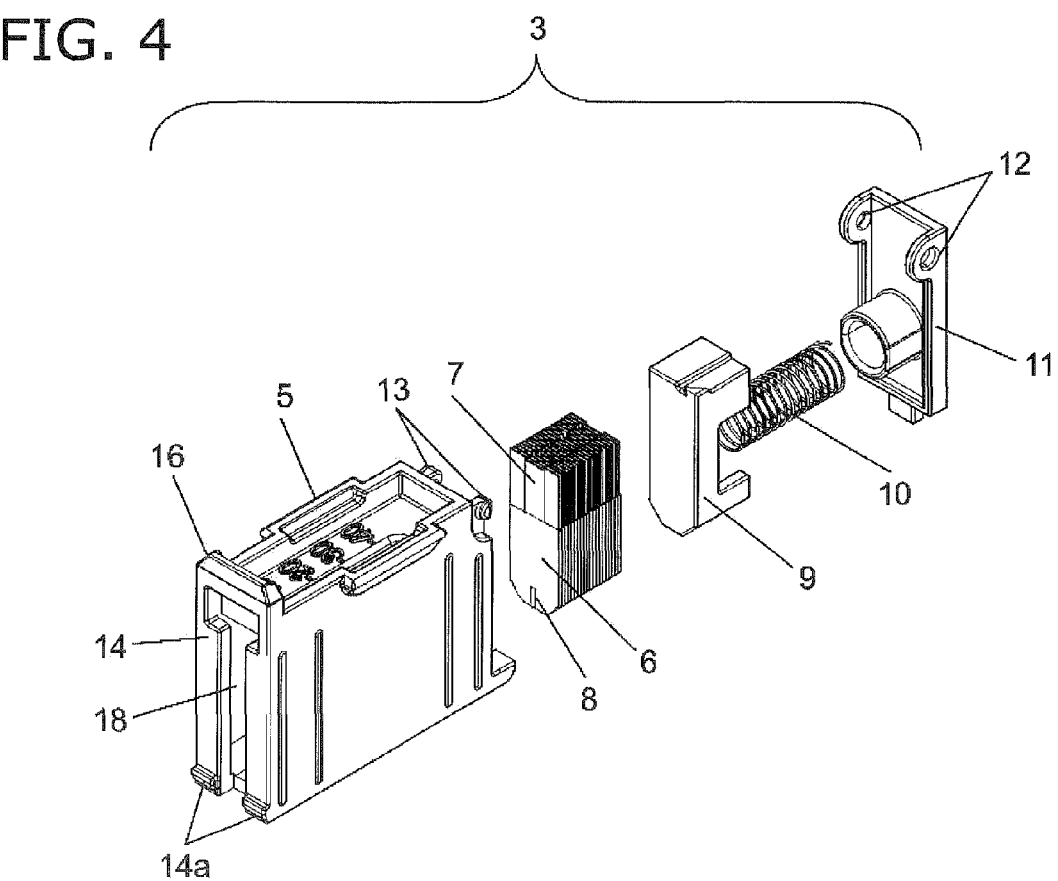
FIG. 4 is an exploded oblique view of the sensor housing container pertaining to the first embodiment of the present invention.

FIG. 4 is an exploded oblique view of the sensor housing body 3.

The sensor housing body 3 has a cuboid sensor case 5. This sensor case 5 comprises a rectangular sensor housing opening 5a (shown in FIG. 5) at one end, and a plurality of thin, rectangular sensors 6 are pushed in through this sensor housing opening 5a. When the sensor case 5 has been housed in the interior of the container 1 as shown in FIG. 1, the sensors 6 inside the sensor case 5 are stacked in a state in which the electrode 7 side is facing the opening side of the container 1 (the upper side in FIG. 4). The sensors 6 are used to measure a blood glucose level, for example, and each has an electrode 7 and a deposit component 8 at the two ends of the sensor main body, which is in a thin, rectangular shape.

As shown in FIG. 4, a sensor platform 9 and a spring 10 (an example of a biasing body) are housed inside the sensor case 5 behind the sensors 6. Engagement protrusions 13 on the sensor case 5 are engaged in engagement holes 12 in a housing lid 11, which closes off the sensor housing opening 5a of the sensor case 5. The spring 10 then biases the stacked sensors 6 by the sensor platform 9 to the side opposite the sensor housing opening 5a of the sensor case 5, that is, to a sensor guide wall 14. The spring-side portion of the sensor platform 9 is provided with a desiccant 9a as shown in FIG. 6, which keeps the inside of the container 1 dry.

Thus, the sensor housing body 3 is made up of the sensor case 5, the sensor platform 9, the spring 10, and the housing lid 11.

Figure 6:
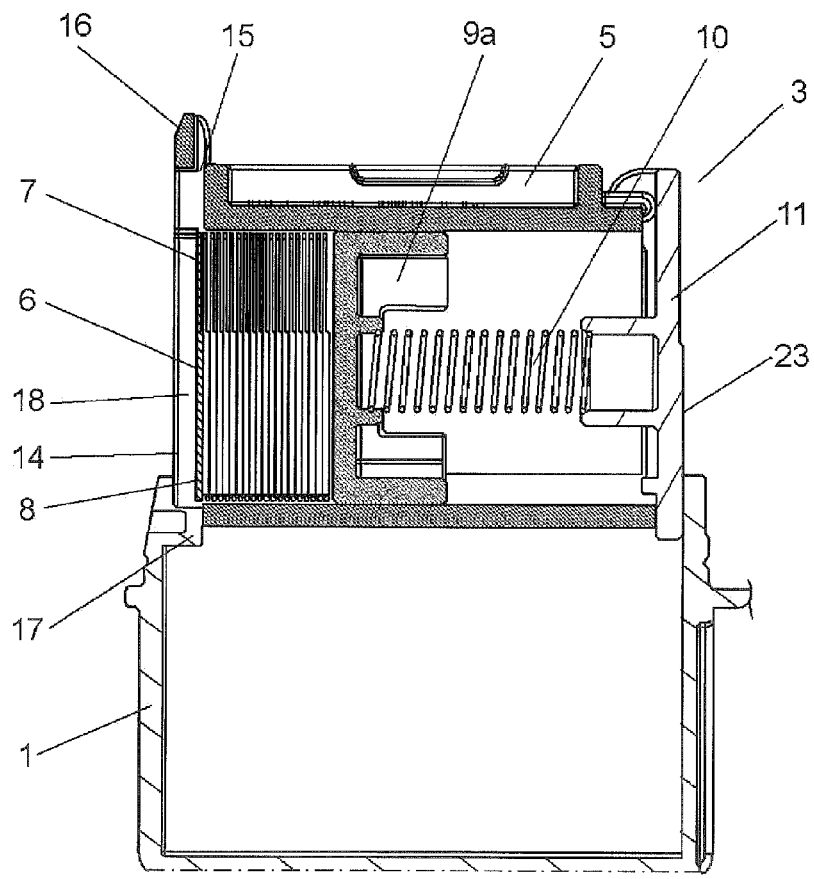
FIG. 6 is a cross section of the sensor housing container pertaining to the first embodiment of the present invention.

FIG. 6 is a cross section of the state when the sensor housing body 3 has been pulled out of the container 1.

The sensor case 5 of the sensor housing body 3 is provided with a sensor discharge port 15 at a position opposite the electrodes 7 of the sensors 6, in the sensor guide wall 14 portion where the sensors 6 are biased by the spring 10, on a face on the opening side of the container 1 (the face on the upper side of the sensor case 5 in FIG. 6). Furthermore, a convex guide protrusion 16 is provided, facing in the discharge direction, on the portion of the sensor case 5 that is on the outside of the sensor discharge port 15 in order to align the sensor discharge port 15 with a sensor insertion port 20a of a measurement device 19 (shown in FIG. 9).

As shown in FIG. 6, the inner face of the container 1 is provided with a push-out protrusion 17 that contacts with the end on the opposite side from the electrodes 7 of the sensors 6, at the portion corresponding to the end on the opposite side from the electrodes 7 of the sensors 6 inside the sensor case 5, in a state in which the sensor case 5 housing the sensors 6 has been pulled out through the opening in the container 1. This push-out protrusion 17 is a substantially cuboid peg that comes into contact with the end of a sensor 6 touching the sensor guide wall 14, out of all the sensors 6 stacked in the interior of the sensor case 5.

As shown in FIG. 4, a groove-shaped guide opening 18 is formed in the sensor guide wall 14 portion of the sensor case 5 corresponding to the push-out protrusion 17, and the push-out protrusion 17 is configured to slide inside the guide opening 18 as the sensor case 5 of the sensor housing body 3 moves in and out of the opening of the container 1.

The guide opening 18 is formed in a groove shape in the sensor guide wall 14, in the center part along the lengthwise direction extending from the bottom face side to the upper face side of the sensor case 5. The width of the guide opening 18 in a direction perpendicular to the lengthwise direction is less than the width of the sensors 6 in a direction perpendicular to the lengthwise direction, so the sensors 6 will not pop out through the guide opening 18, and will be pressed against the inner side of the sensor guide wall 14.

As shown in FIG. 6, the guide protrusion 16 of the sensor case 5 is on the push-out protrusion 17 side of the container 1, that is, the upper part of the sensor discharge port 15 of the sensor case 5. Accordingly, the push-out protrusion 17, the deposit component 8 of the sensors 6, the electrodes 7 of the sensors 6, the sensor discharge port 15, and the guide protrusion 16 are positioned in a straight line in that order from the bottom face of the container 1 toward the opening.

Figure 7:
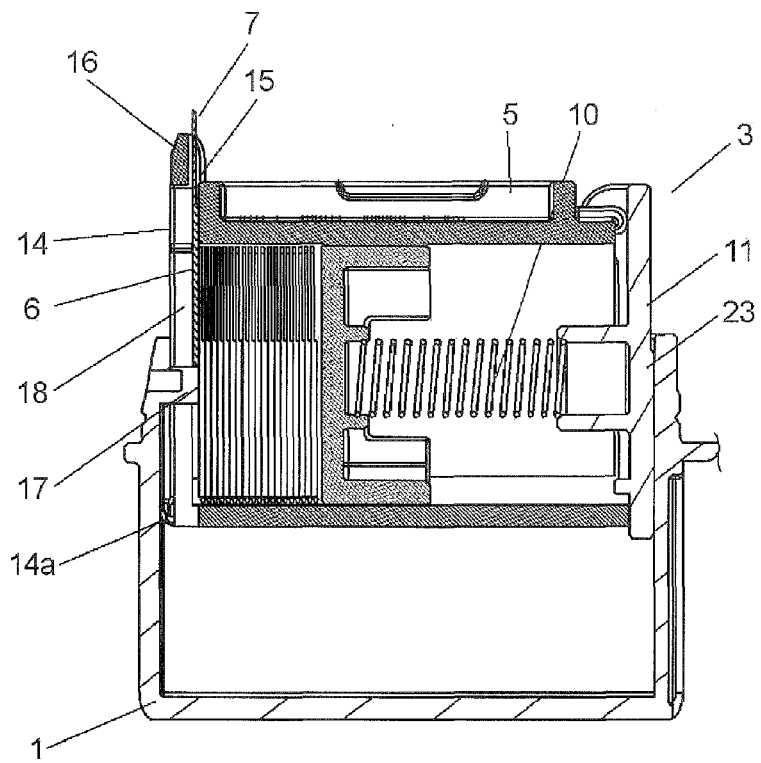
FIG. 7 is a cross section of the sensor housing container pertaining to the first embodiment of the present invention.
Figure 8:
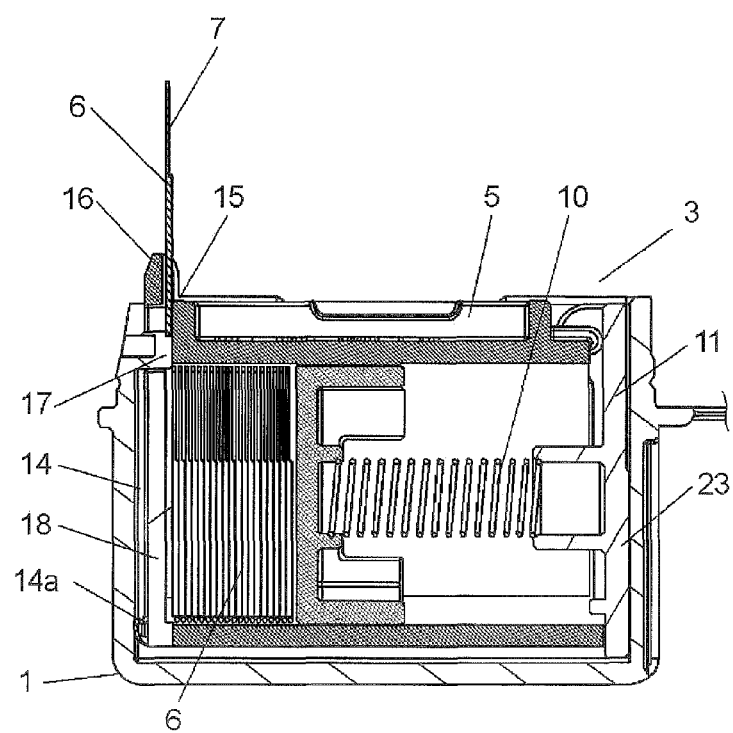
FIG. 8 is a cross section of the sensor housing container pertaining to the first embodiment of the present invention.

Therefore, as shown in FIGS. 7 and 8, as the sensor case 5 is pushed into and housed in the container 1 from a state of having been pulled out of the container 1, the push-out protrusion 17 of the container 1 slides through the guide opening 18 of the sensor case 5 toward the guide protrusion 16.

That is, as the sensor case 5 is housed inside the container 1, the push-out protrusion 17 pushes out the end on the opposite side from the electrodes 7 of the sensor 6 (that is, the end where the deposit component 8 is) to the sensor discharge port 15 side. Then, as shown in FIG. 7, the electrodes 7 of the sensor 6 then moves along the sensor guide wall 14 to the sensor discharge port 15 and the guide protrusion 16, and is discharged from the sensor case 5 as shown in FIG. 8. Upon completion of this discharge operation, the sensor 6 is no longer held in the sensor case 5. Since measurement performance will be degraded if the sensors 6 are in contact with the air for an extended period, the sensor housing body 3 that houses the sensors 6 is closed off by the lid 2 after being pushed in the container 1 as shown in FIG. 3 in order to prevent this deterioration. Consequently, the sensors 6 are housed in a sealed state inside the container 1.

How this configuration is used in this embodiment will now be described.

First, the user rotates the lid 2 from the state shown in FIG. 3, and opens the upper face of the container 1 which had been sealed, as shown in FIG. 1.

Then, the sensor case 5 of the sensor housing body 3 that houses the sensors 6 is pulled up and out of the container 1, going from the state in FIG. 1 to the state in FIG. 2. At this point, two stoppers 14*a* shown in FIG. 4, which are provided on the bottom face side of the sensor housing body 3 on the outer face of the sensor guide wall 14, move toward the opening while being opposite the inner wall of the container 1, as shown in FIGS. 7 and 8. Upon moving toward the opening, the stoppers 14*a* come into contact with stopper pads (not shown) on the opening in the container 1, and this completes the pulling out of the sensor case 5.

As shown in FIG. 6, inside the sensor case 5, the sensors 6 are pressed against the sensor guide wall 14 by the spring 10, and are disposed at a position facing the sensor discharge port 15.

Figure 9:
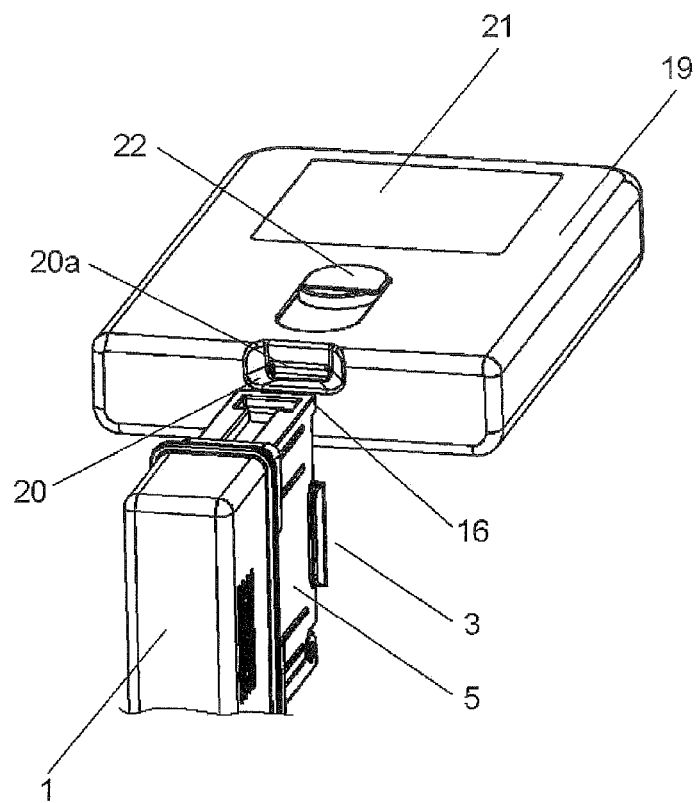
FIG. 9 is an oblique view of the use of the sensor housing container pertaining to the first embodiment of the present invention.

Next, the user uses his right hand, for example, to lift up the measurement device 19 in order to mount the sensor 6 in a sensor insertion component 20 of the measurement device 19, and points the sensor insertion component 20 provided to the measurement device 19 toward himself, as shown in FIG. 9. This sensor insertion component 20 is formed in a concave shape, and the sensor insertion port 20*a* into which the sensor 6 is inserted is provided on the bottom part thereof.

The user rotates the container 1 from which the sensor case 5 has been pulled out, turning it 90 degrees from the state in FIG. 6 to the state in FIG. 9, and lifting it with the left hand, so that the guide protrusion 16 of the sensor case 5 is opposite the sensor insertion component 20 of the measurement device 19.

In this embodiment, the guide protrusion 16 and the sensor discharge port 15 is disposed at the end of the sensor case 5 on the sensor guide wall 14 side, so the user can use the convex guide protrusion 16 provided at the end as a reference to bring it opposite the sensor insertion component 20 of the measurement device 19.

Figure 10:
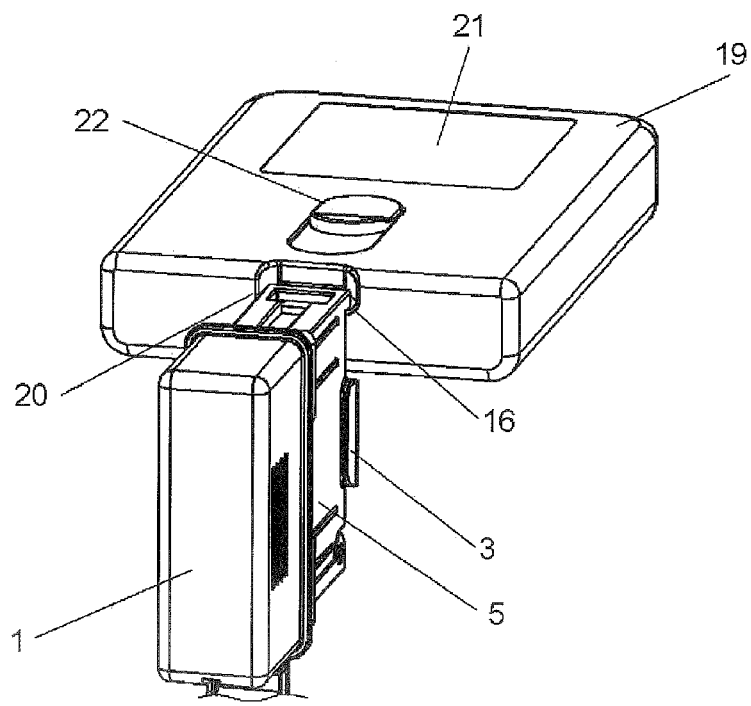
FIG. 10 is an oblique view of the use of the sensor housing container pertaining to the first embodiment of the present invention.

Next, the user aligns the guide protrusion 16 with the concave sensor insertion component 20 as shown in FIG. 10 by bringing his left and right hands closer together in front of him, whereupon the sensor discharge port 15 of the sensor case 5 is opposite the sensor insertion port 20*a* provided in the bottom of the sensor insertion component 20 (this is a substantially aligned state).

Specifically, since the sensor insertion port 20*a* of the measurement device 19 is formed in a narrow shape that prevents water or dust from getting in, it is hard for the user to check visually. However, in this embodiment, if the guide protrusion 16 of the container 1 is aligned with the sensor insertion component 20 of the measurement device 19, this forms a path for the sensor to move from the sensor case 5 into the sensor insertion port 20*a*.

Since the concave shape of the sensor insertion component 20 and the convex shape of the guide protrusion 16 are substantially aligned, the guide protrusion 16 can be securely fitted together with the sensor insertion component 20.

From this aligned state in FIG. 10, when the user presses the container 1 once to the measurement device 19 (brings the container 1 and the measurement device 19 close together), as shown in FIGS. 6 to 8, the push-out protrusion 17 of the container 1 pushes out one sensor 6 that is in contact with the sensor guide wall 14 to the sensor discharge port 15 side. This sensor 6 is pushed out from the electrode 7 side to the sensor movement path. That is, the sensor 6 is pushed through the sensor discharge port 15 to the guide protrusion 16, and then moves into the sensor insertion port 20*a* of the measurement device 19.

Figure 11:
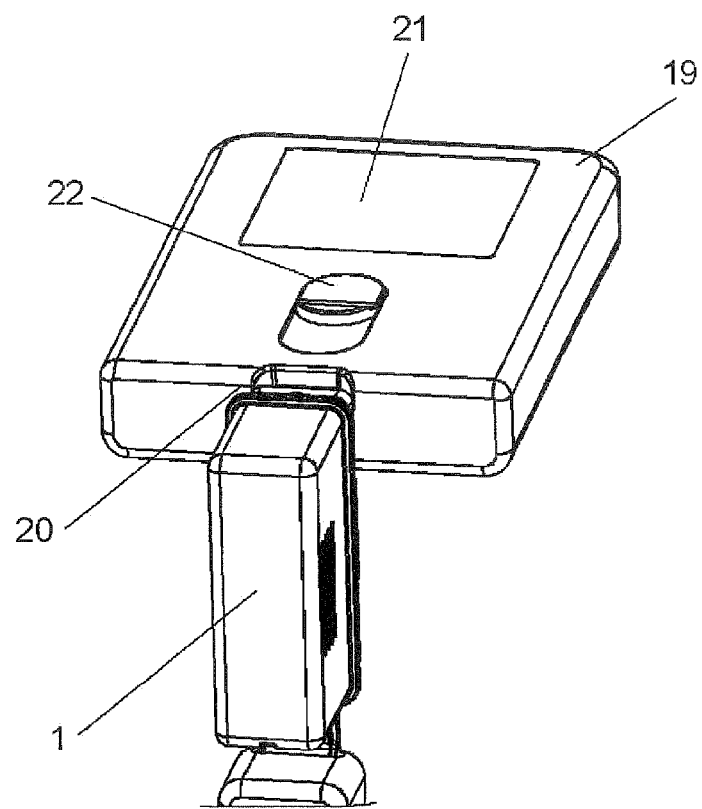
FIG. 11 is an oblique view of the use of the sensor housing container pertaining to the first embodiment of the present invention.

As shown in FIG. 11, when the container 1 is then pushed in all the way toward the measurement device 19, the electrodes of the sensor 6 are mechanically and electrically connected to a connector (not shown) disposed in the back of the sensor insertion port 20*a* inside the measurement device 19, and the sensor case 5 that has been pulled out of the container 1 is put back into the container 1.

That is, just by pressing the container 1 one time to the measurement device 19, the mounting of the sensor 6 is complete, and the housing of the sensor case 5 is also complete.

Therefore, the mounting of the sensor 6 and the housing of the sensor case 5 can be performed at the same time, which makes the device more convenient to use.

Also, in this embodiment, as mentioned above, the guide protrusion 16 of the container 1 is brought into contact with the sensor insertion component 20 of the measurement device 19. Therefore, even when the container 1 has been pushed in all the way toward the measurement device 19, the sensor 6 will not be pushed too far into the connector (not shown) of the measurement device 19, so the sensor 6 can be properly inserted into the connector (not shown).

At this point, since the convex guide protrusion 16 and the concave sensor insertion component 20 are securely fitted together, the container 1 and the measurement device 19 will not come apart, etc., and the sensor 6 will not be accidentally damaged during its insertion.

Figure 12:
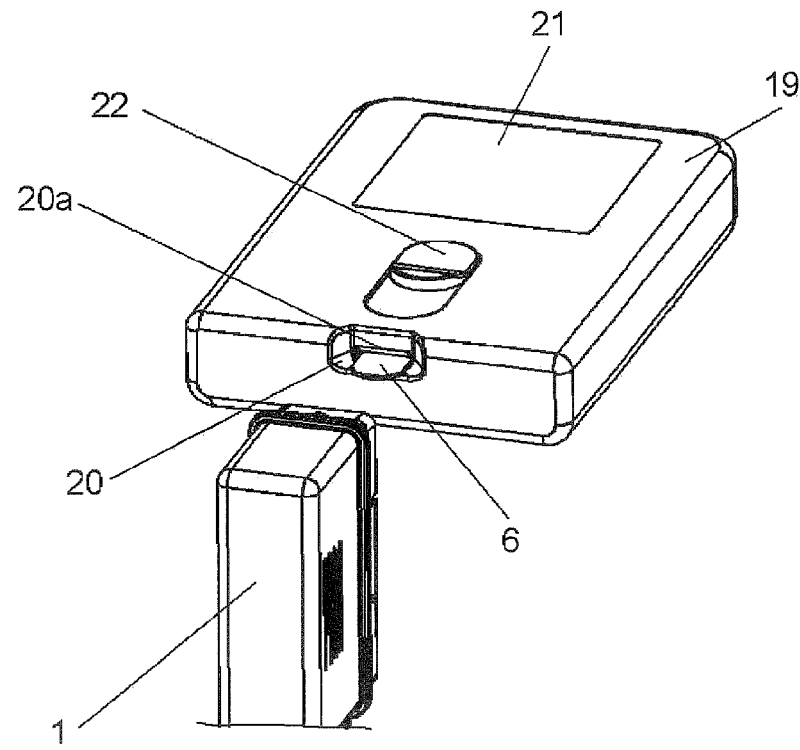
FIG. 12 is an oblique view of the use of the sensor housing container pertaining to the first embodiment of the present invention.

After this, the user separates the container 1 from the measurement device 19, whereupon the sensor 6 is in a state of having been mounted in the measurement device 19 as shown in FIG. 12. When this mounting is complete (that is, when the above-mentioned discharge operation is complete), the sensor 6 is no longer held in the sensor case 5, so the container 1 can be simply pulled away from the measurement device 19.

Finally, when the container 1 is closed off with the lid 2, the remaining sensors 6 housed in the sensor housing body 3 can be sealed up again. This minimizes the deterioration to the sensors 6 caused by moisture.

Specifically, upon completion of the mounting of the sensor 6, the sensors 6 still inside the container 1 can be sealed up again merely by closing the lid 2 to the container 1, and this also makes the device more convenient to use.

Blood is then deposited on the deposit component 8 of the sensor 6 mounted in the measurement device 19, and the measurement device 19 then measures the blood glucose level, the result of which is displayed on a display component 21. When a discharge lever 22 of the measurement device 19 is then operated, the sensor 6 is discharged from the sensor insertion component 20 and discarded.

Also, in this embodiment, as shown in FIGS. 1 to 3, at the opening of the container 1, the lid 2 is openably and closeably linked by the connector 4 to the portion on the opposite side from the push-out protrusion 17 in FIG. 6. Therefore, in the above-mentioned mounting of the sensor 6 in the measurement device 19, the lid 2 is located under the measurement device 19 and the container 1 (the lower side in FIGS. 9 to 12), that is, on the opposite side from the guide protrusion 16 above, and does not get in the way of aligning the guide protrusion 16 with the sensor insertion component 20 (that is, the mounting of the sensor 6 in the measurement device 19).

Since the mounting of the sensor 6 in the measurement device 19 involves merely pressing the container 1 once to the measurement device 19, the user will not accidentally touch the electrodes 7 of the sensor 6 and insert the sensor 6 into the measurement device 19 in a state of having dirt or the like adhering to it. Also, since the user does not touch the sensor 6, the user's body heat is not transmitted to the sensor 6 and therefore does not adversely affect measurement.

This also makes the device more convenient to use.

Also, with a configuration as in this embodiment, in which the sensor case 5 can be pulled out of the container 1, and the push-out protrusion 17 of the container 1 pushes a sensor 6 out of the sensor case 5, there needs to be a small gap between the sensor case 5 and the container 1 in order to pull the sensor case 5 out of the container 1. This gap, however, poses the risk that the push-out protrusion 17 of the container 1 will not properly come into contact with the thin sensor 6 inside the sensor case 5.

Figure 5:
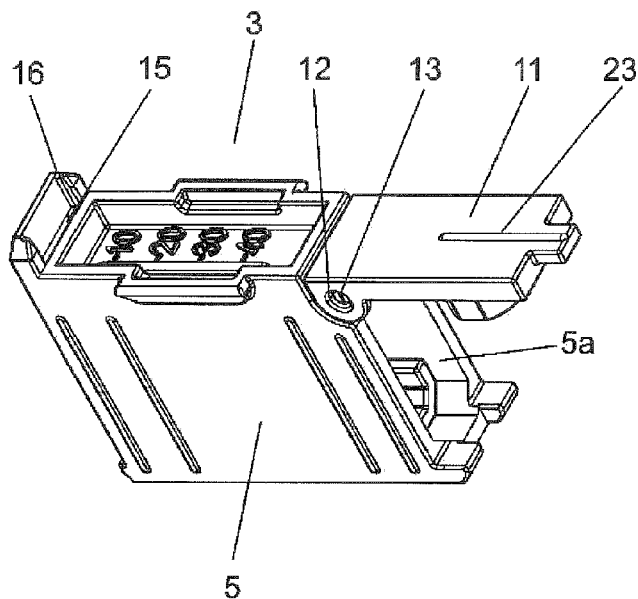
FIG. 5 is an oblique view of the sensor housing body of the sensor housing container pertaining to the first embodiment of the present invention.

In view of this, with the sensor case 5 in this embodiment, as shown in FIG. 5, the side that is opposite the side where the sensors 6 are biased by the spring 10 serves as the sensor housing opening, and the housing lid 11 is provided to openably and closeably cover this sensor housing opening. This housing lid 11 is configured to be connected at one end to the engagement protrusions 13 of the sensor housing opening, provided on the opening side (the upper side in FIG. 5) of the container 1, and the other end is left as a free end. As shown in FIGS. 6 to 8, when the sensor housing opening of the sensor case 5 is closed off by the housing lid 11, the housing lid 11 is biased by the spring 10 toward the outside of the sensor case 5.

Accordingly, inside the sensor case 5, the spring 10 pushes apart the sensor platform 9 and the center portion of the housing lid 11, so the free end of the housing lid 11 is properly pressed against the inner wall of the container 1, and the sensors 6 and the sensor guide wall 14 are properly pressed to the push-out protrusion 17 side of the container 1 by the sensor platform 9.

Therefore, the proper positional relation can be formed between the push-out protrusion 17 of the container 1 and the sensor 6 that contacts with the sensor guide wall 14, and the push-out protrusion 17 can contact with the end of the one sensor 6.

As a result, the push-out protrusion 17 of the container 1 can push out just one sensor 6.

Also, as shown in FIG. 5, a slender pressing protrusion 23 that extends from the free end side to the connector side is provided to the outer surface of the housing lid 11. Accordingly, on the free end side of the housing lid 11, the pressing protrusion 23 comes contact with the inner wall of the container 1, so there is less contact resistance when the sensor case 5 is pulled out of the container 1 than when there is no pressing protrusion 23.

As a result, the sensor case 5 can be easily pulled out of the container 1, and can also be easily pushed in, and this also makes the device more convenient to use.

Figure 13:
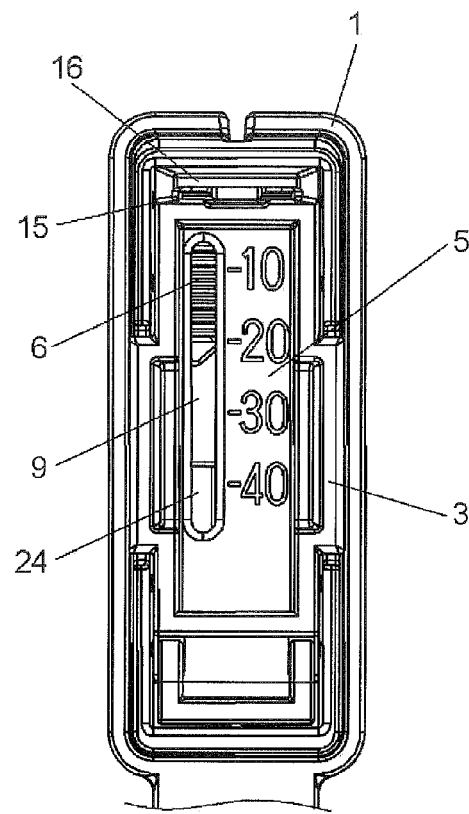
FIG. 13 is a plan view of the sensor housing body of the sensor housing container pertaining to the first embodiment of the present invention.

As shown in FIG. 13, in this embodiment, a remaining sensor confirmation window 24 is provided to the face of the sensor case 5 on the opening side of the container 1. This remaining sensor confirmation window 24 is rectangular in shape and is provided opposite the position where the sensor platform 9 slides through the sensor case 5. A display indicating how many sensors 6 remain is provided near the remaining sensor confirmation window 24.

Accordingly, the user can check how many sensors 6 are left, by the position of the sensor platform 9, which can be seen through the remaining sensor confirmation window 24.

Also, since the color of the sensor platform 9 (such as red) is different from the color of the sensor case 5 (such as white), the user can clearly make out the sensor platform 9 through the remaining sensor confirmation window 24. For example, when there are no more sensors 6, the user will see just the red sensor platform 9, instead of the white sensors 6 that had been visible before. This tells the user that there are no more sensors 6.

The sensor case 5 in this embodiment described above is open at the remaining sensor confirmation window 24 shown in FIG. 13 and the sensor discharge port 15, and also at the guide opening 18 shown in FIG. 4, so it would seem at first glance that the sensors 6 inside the sensor case 5 would be deteriorated by moisture.

In this embodiment, however, as shown in FIG. 3, when the sensor case 5 has been pushed inside the container 1 and the lid 2 closed, the inside of the container 1 is in a sealed state, and this minimizes deterioration of the sensors 6 by moisture.

As described above, the sensor housing container pertaining to this embodiment comprises the container 1 that has an opening, the lid 2 that covers the opening in the container 1 in an openable/closeable manner, and the sensor housing body 3 that can be pulled out of the container 1 through the opening. Also, the sensor housing body 3 has the sensor case 5, which can be pulled out through the opening, and a plurality of flat sensors 6 that are stacked inside the sensor case 5 so that the electrode 7 sides are on the opening side of the container 1. Furthermore, the spring 10 biases the sensors 6 stacked inside the sensor case 5 to one side.

The sensor discharge port 15 is provided to the sensor case 5 at the portion where the sensors 6 are biased by the spring 10 on the face on the opening side of the container 1, and the guide protrusion 16, which is used to align the sensor discharge port 15 with the sensor insertion port 20a of the measurement device 19, is provided to the portion of the sensor discharge port 15 on the outside of the sensor case 5.

Furthermore, on the inner face of the container 1, in a state in which the sensor case 5 has been pulled out through the opening of the container 1, the push-out protrusion 17 that comes into contact with the end of one of the sensors 6 on the opposite side from the electrodes 7 is provided to the portion inside the sensor case 5 that corresponds to the end of the sensors 6 on the opposite side from the electrodes 7, and this also makes the device more convenient to use.

Specifically, in this embodiment, when the user opens the lid 2 to the container 1, which is in a sealed state, and pulls the sensor case 5 housing the sensors 6 out of the container 1, the sensors 6 are disposed at a position opposite the sensor discharge port 15. Next, the user aligns the guide protrusion 16 of the sensor case 5 with the sensor insertion component 20 of the measurement device 19, which forms a path for the sensor 6 to move from the sensor case 5 into the measurement device 19. In this aligned state, when the container 1 is pressed one time to the measurement device 19, this pressing will cause the push-out protrusion 17 of the container 1 to push out a sensor 6 to the sensor discharge port 15 side, and the sensor 6 that is pushed out will then move along the path of the sensors 6 and be mounted at the specified position in the measurement device 19.

That is, the lid 2 of the sealed container 1 is opened and the sensor case 5 housing the sensors 6 is pulled out of the container 1. The guide protrusion 16 of the sensor case 5 is then aligned with the sensor insertion component 20 of the measurement device 19, and the container 1 is merely pressed against the measurement device 19 to mount the sensor 6 in the measurement device. At this point, the sensor case 5 that was pulled out is put back into the container 1.

After this, when the lid 2 of the container 1 is closed, the remaining sensors 6 can be put back in and sealed up.

As a result, the user can easily mount the sensors that are housed in a sealed state in the container to the measurement device, which makes the device more convenient to use.

Second Embodiment

Figure 14:
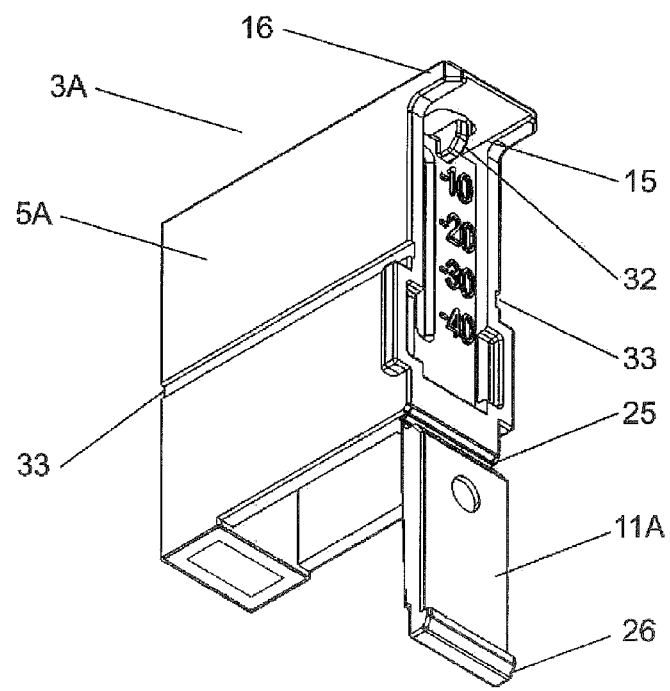
FIG. 14 is an oblique view of the sensor case of the sensor housing container pertaining to a second embodiment of the present invention.

FIG. 14 shows a sensor housing body 3A that is part of the sensor housing container pertaining to a second embodiment of the present invention. The sensor housing body 3A differs from the sensor housing body 3 in the first embodiment of the present invention shown in FIG. 5 in how the housing lid 11 is attached to a sensor case 5A.

More specifically, with the sensor housing body 3A, a housing lid 11A and the sensor case 5A are connected by a bendable connector 25, and are integrally molded from resin along with this connector 25. This reduces the number of parts entailed, and simplifies the production process.

A pull-out stopper 26 used when the sensor case 5A is pulled out of the container 1 is provided to the free end side of the housing lid 11A, on the outer surface of the housing lid 11A. When the sensor case 5A is pulled out through the opening in the container 1 from the state shown in FIG. 15, in which the sensor housing body 3A is housed in the container 1, the pull-out stopper 26 contacts with a stopper 27 provided to the opening of the container 1, and this completes the pulling out of the sensor case 5A.

Also, a desiccant housing chamber 28 is provided inside the sensor case 5A, a desiccant (not shown) is put and housed in this desiccant housing chamber 28 through a desiccant housing opening 29, and then an air-permeable cover (not shown) is affixed to the desiccant housing opening 29. The desiccant housing opening 29 is provided inside the sensor case 5A on the opposite side of the sensor platform 9 from the stacked sensors 6.

Specifically, the desiccant is provided in order to regulate the humidity inside the sensor case 5A; if the humidity is high inside the sensor case 5A, the moisture is absorbed, and conversely, if the inside of the sensor case 5A is dry, moisture is released to adjust the humidity. Particularly when moisture is released, if the sensors 6 are present where this release takes place, the moisture will fall directly onto the sensor 6, which is undesirable.

In view of this, in this embodiment the desiccant housing opening 29 is provided inside the sensor case 5A on the opposite side of the sensor platform 9 from the stacked sensors 6, and this configuration prevents moisture from falling directly on the sensors 6 when it is released from the desiccant, and therefore has the effect of preventing the deterioration of the sensors 6.

A variety of desiccants can be used, such as those in the form of powders or granules, and since an air-permeable cover (not shown) is affixed to the desiccant housing opening 29 as mentioned above, the desiccant will not drop out of the desiccant housing chamber 28. Even if some of the desiccant should for some reason drop out of the desiccant housing chamber 28, it will only drop on the opposite side of the sensor platform 9 from the sensors 6 inside the sensor case 5A. Accordingly, the spilled desiccant will not adhere to the sensors 6 and degrade their performance.

Furthermore, another reason why the desiccant housing opening 29 is provided on the opposite side of the sensor platform 9 from the sensors 6 inside the sensor case 5A is to prevent deterioration of the latter half or the last of the sensors 6 to be used out of the sensors 6 stacked inside the sensor case 5A.

Specifically, in this embodiment, the desiccant housing opening 29 is provided on the opposite side of the sensor platform 9 from the stacked sensors 6 inside the sensor case 5A. With this configuration, since the desiccant housing opening 29 is a short distance from the latter half or the last of the sensors 6 to be used, deterioration of the latter half or the last of the sensors 6 to be used can be effectively prevented.

A cylindrical housing component 9b is provided to the sensor platform 9 to house one end of the spring 10, in the center portion of the face on the opposite side from the stacked sensors 6. Accordingly, when the spring 10 pushes the sensor platform 9 away from the center portion of the housing lid 11A, the sensors 6 will be properly pressed to the sensor guide wall 14 side by the sensor platform 9, and the housing lid 11A will be properly pressed against the inner face of the container 1.

Figure 16:
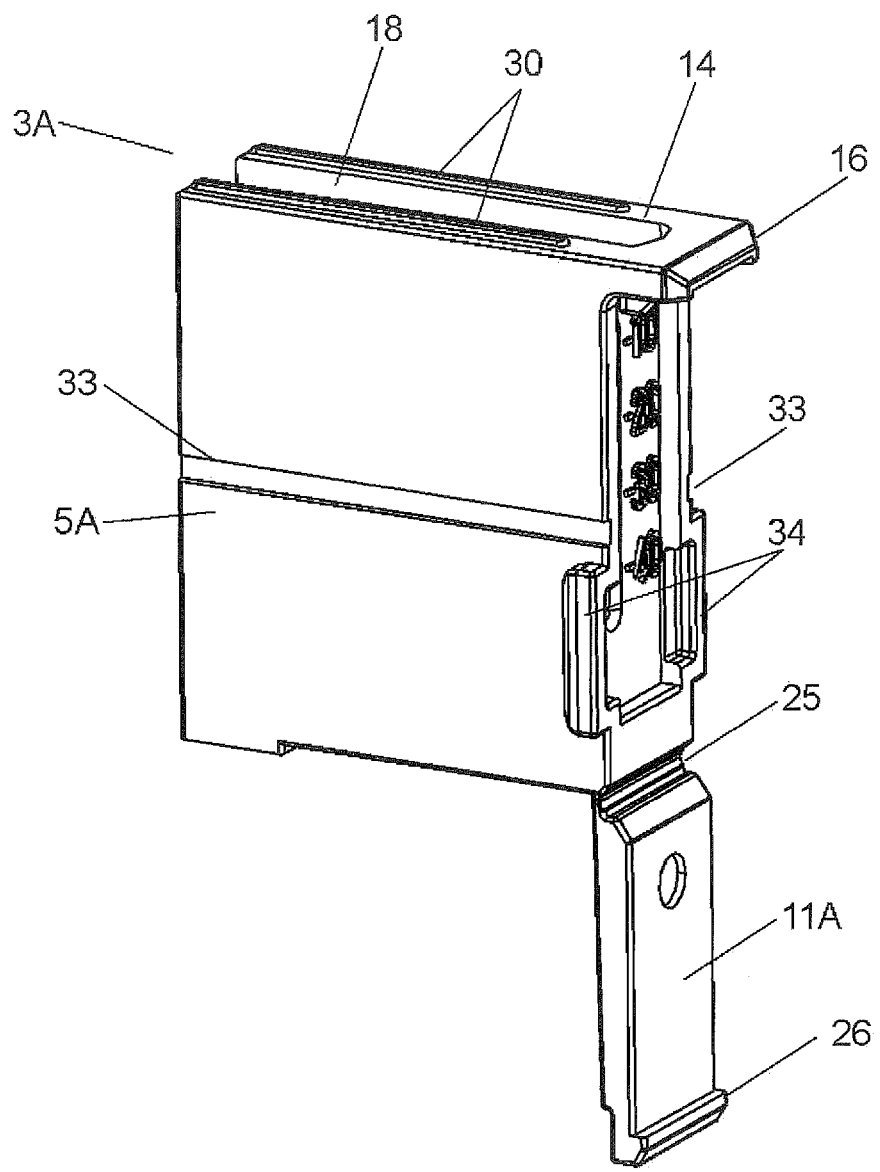
FIG. 16 is an oblique view of the sensor case of the sensor housing container pertaining to the second embodiment of the present invention.

Also, as shown in FIG. 16, two slender contact protrusions 30 are provided to the sensor guide wall 14 portion of the sensor case 5A, along both sides of the groove-shaped guide opening 18. The sensor case 5A slides through the container 1 in a state in which these contact protrusions 30 are in contact with the inner face of the container 1.

Figure 15:
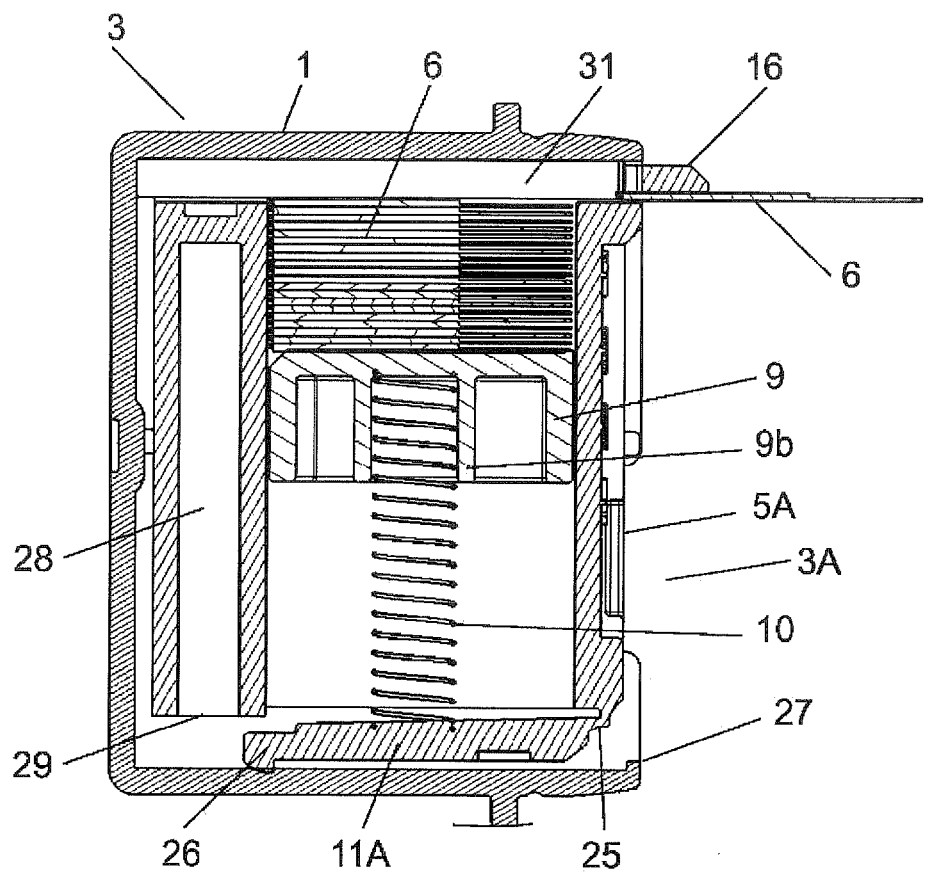
FIG. 15 is a cross section of the sensor housing container pertaining to the second embodiment of the present invention.
Figure 17:
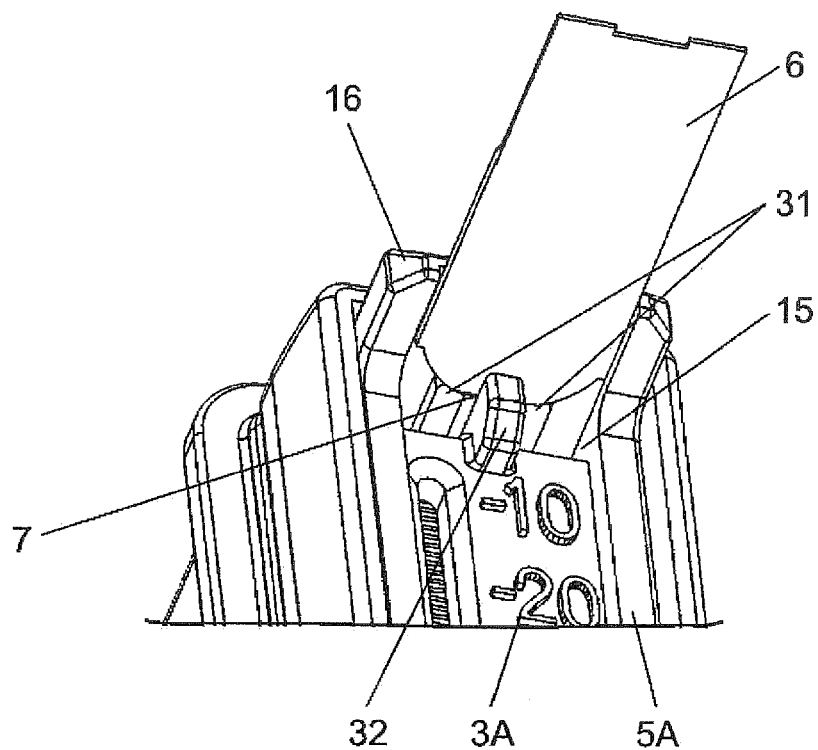
FIG. 17 is an oblique view of the main components of the sensor housing container pertaining to the second embodiment of the present invention.

Also, as shown in FIGS. 15 and 17, two flat, rectangular push-out protrusions 31 that slide through the guide opening 18 are provided along the slender guide opening 18 on the inner face side of the container 1 in a state of having been inserted into the guide opening 18. As shown in FIG. 15, the sensors 6 are pressed against the two push-out protrusions 31 by the spring 10.

The two push-out protrusions 31 provided to the container 1 are arranged such that the ends on the opening side of the container 1 come into contact with both sides of the blood (specimen) deposit component 8 at the end of the sensors 6 on the opposite side from the electrodes 7, as shown in FIG. 17. Accordingly, when the push-out protrusions 31 push a sensor 6 out of the sensor case 5A, the pushing pressure can be prevented from being exerted on the deposit component 8.

Furthermore, the two push-out protrusions 31 are configured so that the side toward the opening of the container 1 is made up of a curved surface corresponding to the shape of the deposit component 8 of the sensor 6, so the sensor 6 can be properly pushed out.

Also, in this embodiment, a sensor receiving protrusion 32 is provided to the sensor discharge port 15 portion of the sensor case 5A at a position corresponding to the guide protrusion 16, flanking the sensor discharge port 15. As shown in FIG. 17, this sensor receiving protrusion 32, the guide protrusion 16, and the two push-out protrusions 31 touch the lower, upper, and side faces of the sensor 6 on the deposit component 8 side of the sensor 6. Accordingly, the sensor 6 will not fall out of the sensor case 5A after the discharge is finished, and will be held in the sensor case 5A.

Therefore, after the sensor 6 has been discharged, it can be easily pulled out in just the direction of the electrodes 7 while being held in the sensor case 5A.

As shown in FIGS. 14 and 16, guide grooves 33 are provided in the direction in which the sensor case 5A is pulled out, in the center part of the outer face of the sensor case 5A. Two guide protrusions (not shown) provided to the container 1 slide in these two guide grooves 33, which allows the sensor case 5A to be pulled out of the container 1 more smoothly.

Also, pull handles 34 are provided between the guide grooves 33 and the housing lid 11A on the face of the sensor case 5A on the opening side of the container 1, so the user can grasp a location close to the housing lid 11A pressed against the inner face of the container 1 and pull the sensor case 5A out, and as a result, the sensor case 5A can be stably pulled out of the container 1.

As discussed above, the sensor housing container of the present invention comprises a container that has an opening, a lid that openably and closeably covers the opening in the container, and a sensor housing body that can be pulled out of the container through the opening, and the sensor housing body is provided with a sensor case that can be pulled out through the opening. Also, inside the sensor case, there are a plurality of flat sensors that are stacked so that their electrode side is on the opening side of the container, and a biasing body that biases the stacked sensors in the sensor case to one side. The sensor case is also provided with a sensor discharge port on the face of the container on the opening side, at the portion where the sensors are biased by the biasing body, and the outer portion of the sensor case of the sensor discharge port is provided with a guide protrusion for aligning the sensor discharge port with the sensor insertion port of a measurement device. Furthermore, the inner face of the container is provided with a push-out protrusion that comes into contact with the end of a sensor on the opposite side from the electrodes, at the portion corresponding to the end of the sensor inside the sensor case on the opposite side from the electrodes, in a state in which the sensor case has been pulled out through the opening of the container.

Specifically, with the present invention, when the user opens the lid of the sealed container and pulls the sensor case housing the sensors out of the container, the sensors are disposed at a position opposite the sensor discharge port. The user then aligns the guide protrusion of the sensor case with the sensor discharge component of the measurement device, forming a path for a sensor to move from the sensor case into the measurement device. When the container is pressed against the measurement device one time in this aligned state, this pressing operation causes the push-out protrusion of the container to push the sensor inside the sensor case out to the sensor discharge port side, and the sensor that is pushed out goes through the sensor movement path and is mounted at a specific position in the measurement device.

That is, the lid of the sealed container is opened and the sensor case housing the sensors is pulled out. The guide protrusion of the sensor case is then aligned with the sensor insertion component of the measurement device, and the container is merely pressed against the measurement device, allowing the sensor to be mounted to the measurement device. The sensor case is put back into the container at this point.

After this, when the lid of the container is closed, the remaining sensors can be put back into a sealed state.

As a result, the user can easily take a sensor from a sealed container and mount it in a measurement device, which makes the device more convenient to use.

INDUSTRIAL APPLICABILITY

The sensor housing container of the present invention is expected to find use as a sensor housing container that houses sensors for measuring blood glucose levels, for example.

The invention claimed is:

1. A sensor housing container, comprising:
    a container including an opening, a first push-out protrusion, and an inner face;
    a lid covering the container, the lid configured to open and close; and
    a sensor housing body configured to be pulled out of the opening when the lid is open;
    the sensor housing body including a sensor case, a plurality of flat sensors, a biasing body, and a sensor discharge port;
    the sensor case configured to be pulled out of the opening;
    the flat sensors disposed stacked inside of the sensor case, each flat sensor including an electrode side and a second side opposite to the electrode side, the flat sensors stacked such that the electrode side is nearest to the opening of the container when the sensor housing body is disposed inside of the container;
    the biasing body biasing the sensors towards a first side of the sensor case;
    the sensor discharge port including a guide protrusion, the sensor discharge port disposed through a face of the sensor case facing the opening when the sensor housing body is disposed inside of the container;
    the guide protrusion disposed on an outer surface of the sensor discharge port, and configured to align the sensor discharge port; and
    the first push-out protrusion disposed on the inner face of the container adjacent to the opening and configured to come into contact with the second side of the flat sensors when the sensor case is pulled out of the opening.

2. The sensor housing container according to claim 1, wherein:
    the sensor case further includes a groove-shaped guide opening;
    the groove-shaped guide opening is disposed corresponding to the first push-out protrusion; and
    the first push-out protrusion is configured to slide through the guide opening.

3. The sensor housing container according to claim 2, wherein:
    the guide protrusion is disposed adjacent to the first push-out protrusion when the sensor case is disposed inside of the container.

4. The sensor housing container according to claim 1, wherein:
    the container further includes a second push-out protrusion;
    each of the flat sensors further includes a specimen deposit component disposed on the second side of the sensors, the specimen deposit component including two sides; and
    the first push-out protrusion and the second push-out protrusion are configured to come into contact with both sides of the specimen deposit component.

5. The sensor housing container according to claim 1, wherein:
the lid is linked to a portion of the opening opposite from the first push-out protrusion.

6. The sensor housing container according to claim 1, wherein:
the sensor case further includes a sensor housing opening, a second side, and a housing lid;
the second side opposite the first side of the sensor housing;
the sensor housing opening disposed on the second side of the sensor housing; and
the housing lid openably and closeably covers the sensor housing opening, and is configured so that the housing lid is biased by the biasing body toward the outside of the sensor case.

7. The sensor housing container according to claim 6, wherein:
the housing lid includes a connector, a first end, and a second end;
the connector connecting the first end of the housing lid to the housing opening, the first end of the housing lid being an end of the housing lid nearest to the opening of the container when the sensor housing body is housed in the container; and
the second end of the housing lid disposed opposite to the first end of the housing lid and being a free end.

8. The sensor housing container according to claim 6, wherein:
the housing lid further includes a pressing protrusion disposed extending from the second end of the housing lid towards the connector on an outer surface of the housing lid.

9. The sensor housing container according to claim 7, wherein:
the housing lid and the sensor case are connected by a flexible connector, and
the housing lid, the sensor case, and the flexible connector are molded integrally together.

10. The sensor housing container according to claim 9, wherein:
the container further includes a stopper disposed adjacent to the opening;
the housing lid further includes a pull-out stopper disposed on the second end of the housing lid; and
the pull-out stopper engages the stopper when the sensor case is pulled out of the container.

11. The sensor housing container according to claim 10, wherein:
the sensor discharge port further includes a sensor receiving protrusion disposed facing the guide protrusion from an opposite side of the sensor discharge port.

12. The sensor housing container according to claim 1, wherein:
the sensor case further includes a remaining sensor confirmation window disposed on a face of the sensor case visible through the opening of the container when the container is open and the sensor case is disposed inside of the container.

13. The sensor housing container according to claim 12, wherein:
the sensor case further includes a sensor platform disposed between the biasing body and the stacked sensors, perpendicular to the sensor confirmation window, and the sensor platform configured to slide in the interior of the sensor case; and
the sensor platform includes a first end that is viewable through the remaining sensor confirmation window.

14. The sensor housing container according to claim 13, wherein:
the sensor platform is a different color from the sensor case.

15. The sensor housing container according to claim 13, wherein:
the sensor case further includes a desiccant housing chamber disposed inside of the sensor case, and the desiccant housing chamber houses a desiccant.

16. The sensor housing container according to claim 15, wherein:
the desiccant housing chamber includes an opening adjacent to the second side of the sensor case.

17. The sensor housing container according to claim 13, wherein:
the container further includes a cylindrical housing that houses one end of the biasing body, the cylindrical housing disposed on an opposite side of the sensor platform from the flat sensors.

18. A sensor attachment method using the sensor housing container according to claim 1, comprising:
opening the lid of a container;
pulling part of a sensor case out of the container through an opening in the container;
aligning a guide protrusion of the sensor case with a sensor insertion port of a measurement device; and
pressing the measurement device and the container together to push a sensor housed in the sensor case into the sensor insertion port of the measurement device.

* * * * *